(12) United States Patent
Palkar et al.

(10) Patent No.: US 11,925,195 B2
(45) Date of Patent: Mar. 12, 2024

(54) SYNERGISTIC NUTRITIONAL COMPOSITIONS FOR TREATING CEREBROVASCULAR DISEASES

(71) Applicant: CELAGENEX RESEARCH (INDIA) PVT. LTD., Thane (IN)

(72) Inventors: Jotiram Palkar, Thane (IN); Rajendra Prasad Tongra, Jaipur (IN)

(73) Assignee: CELAGENEX RESEARCH (INDIA) PVT. LTD., Thane (IN)

( * ) Notice: Subject to any disclaimer, the term of this patent is extended or adjusted under 35 U.S.C. 154(b) by 42 days.

(21) Appl. No.: 17/772,878

(22) PCT Filed: Oct. 31, 2020

(86) PCT No.: PCT/IN2020/050921
§ 371 (c)(1),
(2) Date: Apr. 28, 2022

(87) PCT Pub. No.: WO2021/084559
PCT Pub. Date: May 6, 2021

(65) Prior Publication Data
US 2023/0050208 A1    Feb. 16, 2023

(30) Foreign Application Priority Data
Nov. 1, 2019  (IN) .............................. 201921044292

(51) Int. Cl.
| A23L 33/105 | (2016.01) |
| A23L 33/13  | (2016.01) |
| A61K 31/343 | (2006.01) |
| A61K 31/443 | (2006.01) |
| A61K 31/455 | (2006.01) |
| A61K 36/23  | (2006.01) |
| A61P 9/10   | (2006.01) |

(52) U.S. Cl.
CPC ............. *A23L 33/105* (2016.08); *A23L 33/13* (2016.08); *A61K 31/343* (2013.01); *A61K 31/443* (2013.01); *A61K 31/455* (2013.01); *A61K 36/23* (2013.01); *A61P 9/10* (2018.01)

(58) Field of Classification Search
CPC ........ A61K 31/343; A61K 31/455; A61P 9/10
See application file for complete search history.

(56) References Cited

U.S. PATENT DOCUMENTS

| 8,598,225 B2 | 12/2013 | Feng |
| 2012/0328526 A1 | 12/2012 | Kristian |
| 2017/0204131 A1* | 7/2017 | Szczepankiewicz ..... A61P 3/04 |

FOREIGN PATENT DOCUMENTS

EP    1679070 A1    7/2006

OTHER PUBLICATIONS

Cui et al. (Chinese Medical Journal 2013;126 (18): 3405-3410).*
Yaping Huai,, et al., "L-3-n-butylphthalide protects against vascular dementia via activation of the Akt kinase pathway," Neural Regeneration Research , vol. 8, Issue 19, pp. 1733-1742 (Jul. 2013).
Faezeh Tashakori-Sabzevar, et al., "Evaluation of mechanism for antihypertensive and vasorelaxanteffects of hexanic and hydroalcoholic extracts of celery seed innormotensive and hypertensive rats," Brazilian Journal of Pharmacognosy, vol. 26, pp. 619-626 (Jun. 25, 2016).
Curt Hendrix, "Clinically proven natural alternatives for treating highblood pressure," Hypertension, vol. 2, pp. 1-5 (Feb. 2019).
Haiyan Zhou, et al., "DL-3-n-butylphthalide therapy for Parkinson's disease: A randomized controlled trial," Experimental and Therapeutic Medicine, vol. 17, Issue 5, pp. 3800-3806 (May 2019).
Xi-Qian Chen, et al., "Application and prospects of butylphthalide for the treatment of neurologic diseases," Chinese Medical Journal, vol. 132, Issue 12, pp. 1467-1477 (Jun. 2019).
Bahare Salehi, et al., "Apium Plants: Beyond Simple Food and Phytopharmacological Applications," Applied Sciences, vol. 9, Issue 17, pp. 1-39 (Aug. 29, 2019).
IN Patent Examination Report dated Jul. 29, 2022 as received in Application No. 201921044292.
Iranian Search Report dated Jan. 10, 2023 as received in application No. 140150140003000980.
DI-3-n-Butylphthalide (NBP): A Promising Therapeutic Agent for Ischemic Stroke; Shan Wang et al., Jun. 2018.
Molecules: The In Vivo Therapeutic Potential of NAD-Boosting Evidence; Luis Rajman et al., Mar. 2018.
Gong Bing et al., "Nicotinamide riboside restores cognition through an upregulation of proliferator-activated receptor-[gamma] coactivator 1[alpha] regulated [beta]-secretase 1 degradation and mitochondrial gene expression in Alzheimer's mouse models" Jan. 2013.
Evidence-Based Complementary and Alternative Medicine-2013; Article ID 470975; https ://doi.org/10.1155/2013/470975.

(Continued)

*Primary Examiner* — Bong-Sook Baek
(74) *Attorney, Agent, or Firm* — Maschoff Brennan

(57) ABSTRACT

The present invention disclosed herein relates to synergistic compositions for cerebrovascular diseases. In particular, the invention relates to synergistic, efficient, composition for treating cerebral ischemia or stroke comprising specific combination of standardized celery seed extract (CSE) enriched with Dl-3-N-Butylphthalide (NBP) and SIRT1 activators, wherein D1-3-N-Butylphthalide (NBP) and SIRT1 activator are present in a weight ratio of 1:0.1 to 1:5 along with pharmaceutically acceptable excipients.

3 Claims, 8 Drawing Sheets

(56) References Cited

OTHER PUBLICATIONS

Laeknabladid. May 2014; 100(5) :271-9.
J Stroke. Sep. 2013; 15(3): 128-34.
Stroke Vasc Neurol. Jul. 2019; 4(2): 83-89.
JMed Food. Jun. 2013; 16(6): 558-563.
Progress in Brain Research 245, 2019, 89-118.
Li et al., 2018.
J Neurosci. Jun. 1, 20106,30(24):8180-9.
Acta Pharmacol Sin 2000;21:433-438.
Yao Xue Xue Bao 1995;30:741-744.
Front. Pharmacol. 2020 ; 10 ; 1595.
Zhongguo Yao Li Xue Bao 1998;19:117-120.
Yao Xue Xue Bao 2000;35:408-412.
Stroke. 2008,39:2587-2595.
CNS Neuroscience & Therapeutics 22 (2016) 782-788.
PNAS Oct. 16, 2012 109 (42) 17010-17015.
Trends in Pharmacological Sciences 36(12) 2015.
Stroke. 2015; 46:1966-1974.
Raval et al., 2006, 2008.
Frontiers in Neuroscience, 2018;12;778J.
Annals of Clinical and Translational Neurology 2018; 5(2): 138-146.
PLOS One. 2010; 5(2): e9199.
Qin et al., 2018.

\* cited by examiner

SYNERGISTIC NUTRITIONAL COMPOSITIONS FOR TREATING CEREBROVASCULAR DISEASES

TECHNICAL FIELD OF THE INVENTION

The present invention relates to synergistic nutritional compositions for treating cerebrovascular diseases, preferably the composition is useful for treating cerebral ischemia/stroke.

Further the present invention provides a synergistic, efficient composition comprising specific combination of standardized celery seed extract (CSE) enriched with Dl-3-N-Butylphthalide (NBP) and SIRT1 activator along with pharmaceutically acceptable excipients or carriers.

More particularly, the invention relates to nutritional composition which is useful for treating cerebral ischemia and cerebral stroke to give synergistic effect for stroke recovery.

BACKGROUND AND PRIOR ART

The word cerebrovascular refers to blood flow in the brain. The term cerebrovascular disease includes all disorders in which an area of the brain is temporarily or permanently affected by ischemia, or bleeding, and one or more of the cerebral blood vessels are involved in the pathological process.

Restrictions in blood flow may occur from vessel narrowing (stenosis), clot formation (thrombosis), blockage (embolism) or blood vessel rupture (haemorrhage). Lack of sufficient blood flow (ischemia) affects the brain tissue and may cause a stroke.

Cerebral ischemia is the most common cerebrovascular disease, and it is one of the leading causes of morbidity and mortality worldwide. A transient or permanent local reduction of cerebral blood flow causes cerebral ischemia with a condition of complex pathology. Excitatory amino acid toxicity, oxidative stress, intracellular calcium overload, inflammation, and apoptosis are involved in the pathological process after cerebral ischemic injury. Among these pathological changes, inflammatory response is the most significant, which is mediated by nuclear factor kappa B (NF-κB) signal transduction pathway. Activation of NF-κB promotes proinflammatory cytokines and enzymes including tumor necrosis factor-α (TNF-α), interleukins (ILs), nitric oxide (NO), prostaglandin E2 (PGE2), cyclooxygenase-2 (COX-2), and inducible nitric oxide synthase (iNOS), which may ultimately induce neuronal damage. [*Evidence-Based Complementary and Alternative Medicine*-2013; Article ID 470975; https://doi.org/10.1155/2013/470975].

If damage occurs to a blood vessel in the brain, it will not be able to deliver enough or any blood to the area of the brain that it serves. The lack of blood interferes with the delivery of adequate oxygen, and, without oxygen, brain cells will start to die.

Brain damage is irreversible. Emergency help is vital to reduce a person's risk of long term brain damage and increase their chances of survival.

The World Health Organization (WHO) has defined stroke as, "rapidly developing clinical signs of focal (or global) disturbance of cerebral function, with symptoms lasting 24 hours or longer or leading to death, with no apparent cause other than of vascular origin".

Stroke is an abrupt interruption of constant blood flow to the brain that causes loss of neurological function. The interruption of blood flow can be caused by a blockage, leading to the more common ischemic stroke, or by bleeding in the brain, leading to the more deadly haemorrhagic stroke. Ischemic stroke constitutes an estimated 80 percent of all stroke cases.

Stroke may occur suddenly, sometimes with little or no warning, and the results can be devastating.

Stroke is the most common cause of disability, the second most common cause of dementia and the fourth most common cause of death in the developed world. The incidence of stroke is 150-200/100,000 individuals/year. One among every seven individuals suffers from stroke in their lifetime. [*Laeknabladid.* 2014 May; 100(5):271-9].

According to the World Health Organization, 15 million people suffer from stroke worldwide each year. Of these, 5 million people face death and another 5 million people are permanently disabled.

Stroke is one of the leading causes of death and disability in India. The estimated adjusted prevalence rate of stroke ranges between 84-262/100,000 in rural areas and 334-424/100,000 in urban areas. The incidence rate is 119-145/100,000 based on the recent population based studies. [*J Stroke.* 2013 September; 15(3):128-34]

According to American Association of Neurological Surgeons (AANS) report, stroke is the third leading cause of death in the United States. Among, more than 700,000 people affected every year, about 500,000 of these are first attacks and 200,000 are recurrent ones. About 25 percent of people who recover from their first stroke will have another stroke within five years.

Stroke is a leading cause of serious long-term disability, with an estimated 5.4 million stroke survivors currently alive today. The American Heart Association estimates that in 2003, stroke cost about $51.2 billion in both direct and indirect costs in the U.S. alone.

The most recent prevalence statistics from the American Heart Association estimates that 5,400,000 people have experienced stroke.

Eight of ten strokes are due to cerebral ischemia, and two from cerebral haemorrhage. Cerebral ischemia or brain ischemia is a condition that occurs when there isn't enough blood flow to the brain to meet metabolic demand. This leads to limited oxygen supply or cerebral hypoxia, further leading to the death of brain tissue, cerebral infarction, or ischemic stroke. It is a sub-type of stroke along with subarachnoid haemorrhage and intracerebral haemorrhage.

There are two kinds of ischemia—focal ischemia, which confines to a specific region of the brain and global ischemia, which encompasses wide areas of brain tissue.

Most stroke risk factors are lifestyle related. Lifestyle factors that increase risk of stroke include high blood pressure, smoking, diabetes, high blood cholesterol levels, heavy drinking, high salt and high fat diet and lack of exercise. Other stroke risk factors, such as gender, age and family history, are those that cannot be controlled.

In addition, medical factors including previous transient ischemic attack (TIA) or stroke, ischemic heart disease, atrial fibrillation, and glucose intolerance, all increase the risk of stroke. At a population level, blood pressure is the most important modifiable risk factor for stroke.

The complications after stroke are the medical, emotional and neurological problems that can affect a survivor after a stroke event. In one study, 85% of patients hospitalized for stroke experienced at least one complication following the stroke. A survivor may experience major or minor complications, depending on the severity of the stroke and other factors.

Post-stroke treatment is critical because of the risk of permanent neurological damage, paralysis, or otherwise loses of motor control over different parts of the body.

This is because a stroke will often cut off the circulation of blood to the brain, and depending upon which part of the brain doesn't get blood flow, those parts of the body that these brain locations control can become damaged.

Stroke can also impair memory and learning. These are also byproducts of blood flow being temporarily cut off from critical brain centres.

Recovery time after a stroke is different for everyone-it can take weeks, months, or even years. Some people recover fully, but others have long-term or lifelong disabilities.

Most people will need stroke rehabilitation (rehab) to help them recover after they leave the hospital.

Therefore, there is an urgent need for developing new and effective therapies for stroke patients. Stroke has a complex pathophysiology, which can cause a cascade of injury reactions with eventually cell death after the onset. Many previous studies have focused on the stroke injury mechanisms of excitotoxicity, oxidative and nitrosative stress, and inflammation to develop neuroprotective agents against stroke. However, these therapeutic strategies are still in the preclinical-to-clinical transition. Targeting the endogenous defence mechanisms against stroke has been received attention in the recent decade and considered as a novel target of stroke treatment. [*Stroke Vasc Neurol.* 2019 July; 4(2): 83-89]

Celery seeds have been used in traditional Chinese medicine for a number of health concerns particularly ones relating to cardiovascular functions like lowering high blood pressure.

U.S. Pat. No. 6,761,913 discloses ethanolic extracts of celery seeds for the prevention and treatment of pain, inflammation and gastrointestinal irritation.

One of the chemical constituents of celery seed oil 'N-Butylphthalide' (NBP) is a primary contributor to the flavor and aroma of celery and it is this compound that is believed to be responsible for the antihypertensive effects [*J Med Food.* 2013 June; 16(6): 558-563].

NBP is an extract from *Apium graveolens*, Chinese celery and dl-NBP is a synthesized compound that is neuroprotective in several diseases [*Progress in Brain Research* 245, 2019, 89-118]. The NBP is an approved anti-ischemic stroke drug in China and is quite safe in humans after long time administration [Li et al., 2018; Qin et al., 2018].

In recent years, the inventors have found that racemic butylphthalide (or butylphthalide, NBP) is a drug that has significant therapeutic effects on acute ischemic cerebral stroke.

3-N-Butylphthalide (NBP), an extract from the seeds of *Apium graveolens* Linn (Chinese celery), was synthesized and it received approval by the State Food and Drug Administration of China for clinical use in stroke patients in 2002.

NBP is a chiral compound, which contains both L- and D-isomers. Peng et al. [*J Neurosci.* 2010 Jun. 16; 30(24): 8180-9] found that L-3-n-butylphthalide (L-NBP) attenuates learning and memory deficits induced by chronic cerebral hypoperfusion in rats.

U.S. Pat. No. 8,598,225B2 discloses chemical resolution of racemic butylphthalide (dl-NBP), where levo-butylphthalide and dextro-butylphthalide are obtained separately.

Cerebral ischemia is induced when there is not enough blood flowing to the brain. In this case, the blood cannot meet the metabolic needs. When the brain is hypoxic, it is found that the cerebral metabolism changes and the metabolic rate decreases. This results in the death of brain tissues or ischemic stroke.

NBP has the ability to decrease the area of cerebral infarct in focal cerebral ischemic rats [*Acta Pharmacol Sin* 2000; 21:433-438]. It can also improve energy metabolism in mice with complete brain ischemia [*Yao Xue Xue Bao* 1995; 30:741-744].

The positive effects of NBP and L-NBP on cerebral ischemia and cerebral infarct have been verified in ischemic patients and animal models; however, little is known about the neuroprotective machinery of NBP.

Yanping Wang et al in his study provides evidence that dl-NBP treatment could also promote functional recovery after focal transient ischemia stroke, and this recovery is associated with upregulated white matter integrity, microvessels, and the tight junction protein occludin. Further results have been suggested that, in future, dl-NBP may also be applied in clinic to promote functional recovery during the later phase of focal transient ischemic stroke [*Front. Pharmacol.* 2020; 10; 1595].

Mitochondria play a crucial role in apoptosis. NBP also increases the ATP level in rats with cerebral ischemia, and therefore prevents mitochondrial dysfunction resulting from ATP depletion [*Zhongguo Yao Li Xue Bao* 1998; 19:117-120].

Xiong and Feng [*Yao Xue Xue Bao* 2000; 35:408-412] found that NBP improved mitochondrial dysfunction during cerebral ischemia.

NAD is an essential cell survival factor that participates in various critical cellular processes, including energy metabolism, ADP-ribose cyclase synthesis, and class III histone deacetylase activity. A large body of literature shows that cerebral ischemia/reperfusion results in PARP-1 overactivation and consequent decline of NAD levels in the brain. As NAD is essential for the mitochondrial electron transport reaction, NAD depletion is thought to suppress mitochondrial function and ATP generation, leading to the release of apoptosis-inducing factor (AIF) and eventually cell death. Thus, neuronal NAD elevation is crucial for cell survival [*Stroke*. 2008; 39:2587-2595].

The neuroprotective effects of NAD replenishment, either through exogenous NAD delivery or endogenous NAD biosynthesis, and the underlying mechanisms for NAD neuroprotection, may enhance the candidacy of NAD as a novel therapeutic strategy for stroke.

Nicotinamide phosphoribosyltransferase (NAMPT), the rate limiting enzyme for mammalian nicotinamide adenine dinucleotide (NAD) salvage synthesis, has been elucidated as a new therapeutic target of ischemic stroke.

Researchers have demonstrated both endogenous NAMPT overexpression and extracellular NAMPT treatment protect against neuronal injury in oxygen—glucose deprivation (OGD) and middle cerebral artery occlusion models (MCAO). Moreover, inhibition of NAMPT accelerates stroke occurrence and death in stroke-prone spontaneously hypertensive rat, indicating the role of NAMPT in stroke prevention.

Based on the protective role of NAMPT in stroke, therapeutic intervention using NAMPT activators is promising for treatment against stroke. Although many novel NAMPT activators have been discovered recently, such as an aminopropyl carbazole derivative which protects against neuronal injury, reduces cerebral infarction, and upregulates brain NAD levels upon ischemic stress [*CNS Neuroscience & Therapeutics* 22 (2016) 782-788]. However, further studies need to be carried out to characterize stereochemistry of active analogue of aminopropyl carbazole for clinical development [*PNAS* Oct. 16, 2012 109 (42) 17010-17015].

Therefore, the present inventors have come up with NAMPT activators which are extracted from natural source i.e., celery seeds. Moreover, the celery seed extract (CSE) enriched with NBP is used as NAMPT activator for stroke recovery.

Besides, the role of NAMPT in stroke is only explored as monotherapy. It is still unclear whether NAMPT-based combination therapy with other neuroprotective agent or anti-inflammatory treatment is more effective to cure stroke.

According to P. Wang et al. [*Trends in Pharmacological Sciences* 36(12) 2015] NAMPT metabolic pathway connects NAD-dependent sirtuin (SIRT) signaling, constituting a strong intrinsic defense system against various stresses.

Therefore, only the enrichment of NAD is not enough for the neuronal survival and functioning in stroke salvage. There must be need of SIRT1 activators to augment endogenous defense mechanism for stroke recovery.

The present inventors have performed extensive research for developing synergistic combination therapy of NAMPT with SIRT1 activators through salvage pathway, wherein the nutrient based ingredients not only regenerated damaged areas in the brains but also converted structural cells into functioning neurons.

Sirtuins, a family of NAD-dependent deacetylases, regulate neurogenesis. Most of biological functions of NAMPT-NAD cascade are mediated by sirtuins, including SIRT1 for neuroprotection against acute cerebral ischemia [*Stroke*. 2015; 46:1966-1974].

Initial studies have reported that treatment with resveratrol shows neuroprotective effects in OGD in organotypic hippocampal slices and global cerebral ischemia in rats [Raval et al., 2006, 2008].

Moreover, the combination treatment with SIRT1 activators and NAD may provide a synergetic strategy that contributes to neuroprotection [*Frontiers in Neuroscience*, 2018; 12; 778]. SIRT1 is a promising therapeutic target for ischemic stroke for attenuating ischemic stress and improving stroke outcome.

The mammalian target of rapamycin (mTOR) pathway plays an essential role in a number of important physiological functions including cell growth, proliferation, protein synthesis, metabolism, and autophagy. mTOR is involved in the regulation of several diseases, cellular functions, and trauma in the CNS. In the brain, the mTOR pathway regulates synaptic plasticity, neuronal transmission, axon outgrowth, neuronal size, and spine morphology, thus loss of homeostasis of mTOR pathway is involved in a variety of neurologic diseases such as epilepsy, Alzheimer's disease and Parkinson's disease.

Numerous reports have demonstrated that mTOR pathway is involved in brain ischemia-reperfusion induced injury. It was observed that mTOR signaling pathway is abnormally activated in ischemic penumbra and inhibited in ischemic core after middle cerebral artery occlusion (MCAO). Increased apoptosis and decreased autophagy activity were demonstrated both in ischemic penumbra and ischemic core.

Further the researchers found that upregulating the mTOR pathway in ischemic core and downregulating the mTOR pathway in ischemic penumbra may benefit the treatment of ischemia-reperfusion injury [*Annals of Clinical and Translational Neurology* 2018; 5(2): 138-146].

Since the neurons in ischemic core are difficult to rescue, there is need to find out a potent and efficient nutrient to suppress the over activation of mTOR in ischemic penumbra, a zone which can be transferred to normal zone under appropriate treatment.

Intriguingly, it was observed that both SIRT1 and mTOR have been linked to age-associated diseases with SIRT1 activation having a protective effect, whereas inhibition of mTOR confers a beneficial effect. Autophagy, a mechanism important in regulating stress response and aging is negatively regulated by mTOR, whereas SIRT1 has been reported to activate autophagy by deacetylating several essential components of the autophagy machinery. The inverse relationship between the roles of SIRT1 and mTOR in aging-associated diseases and lifespan extension suggests a functional interrelationship between these two proteins.

SIRT1 and mTOR signaling pathways are indeed interconnected in a way that promotes stress sensing pro-survival signals, where the regulation of mTOR is mediated potentially through an interaction of SIRT1 with the TSC1-TSC2 complex [*PLoS One*. 2010; 5(2): e9199].

The present inventors have demonstrated that SIRT1 activation and mTOR inhibition is improved through exogenous biologically active agent that promotes autophagy, attenuates ischemia-induced neuronal death, and reduces ischemic brain damage.

In view of the above prior art, monotherapy comprising either NAMPT activators or SIRT activators or NAD precursors does not lead to significant results in the ischemic patients. Moreover, for better therapeutic results the combination therapy with synergistic effect is extremely demanded for large population suffering with ischemic stroke.

Therefore, the present inventors have developed potent, safe and cost effective synergistic combination of protein activators which not only enhances endogenous NAD+ bioavailability; but also promotes cell survival and function by modulating cellular signaling pathway.

Objective:

The primary object of the invention is to provide a nutritional composition for improving the conditions related to stroke recovery; preferably cerebral ischemia/stroke.

Further object of the invention is to provide a combination of therapeutically active, natural, non toxic, safe ingredients for treating cerebral ischemia.

Another object of the invention is to provide a combination of therapeutically active natural ingredients that work synergistically to increase the expression of protein enzymes necessary for up regulation of NAD level.

Yet another object of the invention is to provide combination of therapeutically active natural ingredients that work synergistically for neuroprotection through cellular signaling pathway.

Yet another object of the invention is to provide combination of therapeutically active natural ingredients or nutrients that work synergistically by improving blood flow recovery and modulating inflammation in ischemic brain tissues.

Yet another object of the invention is to provide a synergistic combination of celery (*Apium graveolens* L) seed extracts enriched with Dl-3-N-Butylphthalide (NBP), along with SIRT1 activator, for treating cerebral ischemia and cerebral stroke.

Another object of the invention is to provide therapeutically effective, safe, herbal remedy for treating cerebral ischemia through site specific action with no adverse effects.

SUMMARY

To meet the above objectives, the inventors of the instant invention carried out thorough experiments to establish significant effect of the bioactive ingredients, or nutrients, or natural substances, or extracts, or chemical constituents, or phytoconstituents, present in the composition that protects against ischemia induced energy depletion and ameliorate cell survival and functioning in a subject suffering from neurological diseases like cerebral ischemia.

In particular aspect, the invention relates to synergistic nutritional compositions comprising therapeutically active nutrients along with pharmaceutically acceptable carriers for treating cerebral ischemia or related conditions.

In another aspect, the invention provides hybrid neuroprotective therapy which comprises synergistic combination of celery (Apium graveolens L) seed extracts and SIRT1 activators along with pharmaceutically acceptable carriers.

In yet another aspect, the invention provides synergistic nutritional composition comprising exogenous blend of celery (Apium graveolens L) seed extract enriched with Dl-3-N-Butylphthalide (NBP) and SIRT1 activators along with pharmaceutically acceptable carriers.

In another particular aspect, the present invention provides synergistic nutritional compositions for improving cerebrovascular disease worldwide comprising specific combination of celery seed extract containing 40-90% Dl-3-N-Butylphthalide (NBP) and NAD+ precursors such as Nicotinamide Riboside (NR), Nicotinic Acid (NA), Nicotinamide (NAM); nicotinamide derivatives such as Nicotinamide Mononucleotide (NMN) and N(1)-Methylnicotinamide (1 -MNA).

In one particular aspect the present invention provides nutritional neuroprotective composition comprising synergistic combination of 3-N-Butylphthalide (NBP) and Nicotinamide riboside (NR) salt, which are present in therapeutically effective amount.

In further aspect, the present invention provides synergistic nutritional composition, wherein the bioactive moieties are present in specific weight ratio, where they act synergistically for treating cerebrovascular diseases.

According to the invention, 3-N-Butylphthalide (NBP) increases expression of NAMPT and BDNF through salvage pathway; simultaneously Nicotinamide riboside (NR) modulates the mTOR activation/signaling pathway.

Notably NBP induced NAMPT activation through salvage pathway improves endogenous defense system by elevating NAD level after stroke and protects against ischemia-induced energy depletion, neural cell death, and eventually brain infarction. It further enhances brain capillary density, increases number of proliferating endothelial cells and improves blood flow recovery. Further NBP induced BDNF activation modulates local inflammation in ischemic brain tissues on the cellular, cytokine, and transcription factor levels.

The co-administration of SIRT1 activators like NR decreases mTOR activation and infarct volume through inhibition of neuron apoptosis and activation of autophagy that subsequently improve neurological function.

In one more aspect, the invention provides combination of naturally occurred nutrients for improving neurological disorders without any adverse effect, wherein therapeutically effective amount of NBP or pharmaceutically acceptable salts thereof is co-administered with NR, optionally in presence of bioenhancer.

In another aspect, the invention provides cost effective, non-toxic, efficient and environmentally safe composition comprising synergistic combination of nutrients for treating cerebral ischemia induced diseases or conditions without any adverse effect.

In yet another aspect, the invention relates to synergistic nutritional compositions comprising combination of standardized celery seed extract in the rage of 10-500 mg comprising 40-90% racemic NBP or salts thereof and NR present in the range of 1-500 mg; along with pharmaceutically acceptable excipients/carriers, optionally in presence of bioenhancer.

In one more aspect, the invention discloses synergistic nutritional composition which is useful for treating cerebrovascular diseases such as cerebral ischemia, brain ischemia, cerebral infarction, cerebral stroke, cerebral edema, postischemic stroke, acute ischemic stroke, hemorrhagic stroke, transient ischemic attacks (TIA), cerebral hypoxia, aneurysm, vascular malformation, cryptogenic stroke and like thereof.

Abbreviations mTOR: Mammalian target of rapamycin
BDNF: Brain-derived neurotrophic factor
NAMPT: Nicotinamide phosphoribosyltransferase
$NAD^+$: Nicotinamide adenine dinucleotide
CSE: Celery seed extract
NR: Nicotinamide riboside
NBP: DL-3-N-Butylphthalide
SIRT1: Sirtuin (silent mating type information regulation 2 homolog) 1
MCAO: Middle cerebral artery occlusion
OGD: Oxygen glucose deprivation

DETAILED DESCRIPTION

Figure 1:
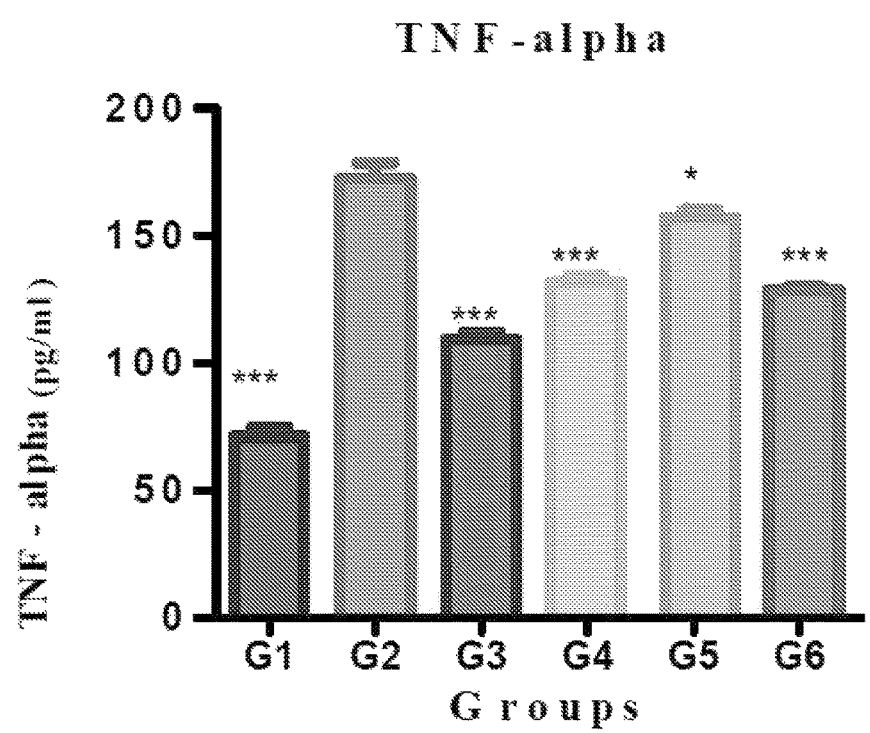
FIG. 1 illustrates the effect of test substances on Rat TNF alpha levels.

The invention will now be described in detail in connection with certain preferred and optional embodiments, so that various aspects thereof may be more fully interpreted and comprehended. However, any skilled person in the art or artisan will appreciate the extent to which such embodiments could be generalized in practice.

It is further to be understood that all terminology used herein is for the purpose of describing particular embodiments only, and is not intended to be limiting in any manner or scope.

Unless defined otherwise, all technical and scientific expressions used herein have the same meaning as commonly understood by one of ordinary skill in the art to which embodiments of the invention pertain.

In describing and claiming the embodiments of the present invention, the following terminology will be used in accordance with the definitions set out below which are known in the art.

The singular forms "a" "an" and "the" include plural reference unless the context clearly dictates otherwise. Also, the term "composition" does not limit the scope of the invention it may include multiple compositions illustrations to establish best mode of the invention.

The term "pharmaceutically/nutraceutically acceptable salt," as use herein, represents those salts which are, within the scope of sound medical judgment, suitable for use in contact with the tissues of humans and animals without undue toxicity, irritation, allergic response and the like and are commensurate with a reasonable benefit/risk ratio. Particularly the term "pharmaceutically-acceptable salts" refers to the relatively non-toxic, inorganic and organic acid addition salts of compounds, alkali or alkaline earth metal salts, as well as solvates, co-crystals, polymorphs, isomers, enantiomers, congeners and the like of the salts.

In a preferred embodiment, the invention relates to nutritional compositions comprising synergistic combination of standardized celery seed extract (CSE) enriched with NBP constituent and SIRT1 activators, particularly NR and/or pharmaceutically acceptable salts thereof.

In another preferred embodiment, the invention provides synergistic nutritional compositions comprising specific combination of bioactive ingredients, wherein one ingredient is phytoconstituent NBP derived from celery seed extract.

The term 'extract' or 'fraction' refers to substance or an active substance with desirable properties that is removed or extracted from the aerial or non-aerial parts of a plant, usually by treating it with organic or non-organic solvent or water or mixtures thereof to be used for a particular purpose.

In the present invention the celery seeds are extracted by using simple, fast, economically viable extraction process known in the art.

*Apium graveolens* (Celery) is a plant in the family Apiaceae that has been cultivated as a vegetable since antiquity; its extracts are used in medicines. Dl-3-N-butylphthalide (NBP) is derived from the seeds of *Apium graveolens* and was shown to improve the outcomes of cerebral infarction by increasing the number of capillaries in the ischemic region, promoting the establishment of collateral circulation, enhancing cerebral blood flow, protecting the mitochondria, improving the cerebral energy metabolism and narrowing the infarction area, among other effects [*Neurochem Int* 2012; 60: 134-44].

Several multicenter, open-label clinical studies on NBP for the treatment of acute ischemic stroke showed that NBP was both effective and safe.

3-N-butylphthalide (NBP) comprises a family of optical isomers that includes 1-3-N-butylphthalide (1-NBP), d-3-N-butylphthalide (d-NBP), and dl-3-N-butylphthalide (dl-NBP). L-NBP is one of the chemical constituents in celery oil, whereas dl-NBP is synthetic and an important neuroprotective drug for the treatment of neurologic diseases. Dl-NBP is a fat-soluble substance that can freely pass across the blood-brain barrier.

Further 3-N-butylphthalide (NBP) may also be known as (+/−)-butylphthalide, Butylphthalide, 3 -n-Butylphthalide, 3-Butylisobenzofuran-1(3H)-one, 3-Butylthalide, 3-N-Butylphthalide, 3-N-butyl-phthalide, butylphthalide, n-Butylphthalide. It has molecular formula $C_{12}H_{14}O_2$, represented by Formula I.

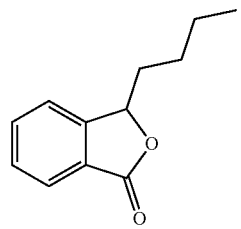

Formula I

In the present invention, the standardized celery seed extract enriched with 40-90% of 3-N-Butylphthalide (NBP), preferably 80-90% is procured from China.

In another preferred embodiment, the invention provides nutritional composition comprising celery extract enriched with NBP, wherein the effective dosage of NBP enhances expression of NAMPT and BDNF in brain.

It is noteworthy that NBP induced NAMPT activation through salvage pathway improves endogenous defense system by elevating NAD level after stroke and protects against ischemia induced energy depletion, neural cell death, and eventually brain infarction. It further enhances brain capillary density, increases number of proliferating endothelial cells and improves blood flow recovery.

Similarly, NBP induced BDNF activation modulate local inflammation in ischemic brain tissues on the cellular, cytokine, and transcription factor levels.

In another embodiment, the effective dosage of NBP results in an increased number of capillaries in the ischemic region, promotes the establishment of collateral circulation, protect the mitochondria, and narrow the infarction area, among other effects.

In yet another embodiment, the invention provides synergistic nutritional composition wherein the average effective dose of celery seed extract enriched with NBP is estimated in the range of 10-500 mg which comprises 40-90% racemic NBP of total composition.

In another embodiment, the invention provides hybrid or concomitant or combination therapy for treating cerebral ischemia, wherein other active moiety is SIRT1 activator(s) that gives synergistic effect to the composition by attenuating ischemia-induced neuronal death, and reducing ischemic brain damage.

In yet another embodiment, the invention provides synergistic nutritional composition wherein SIRT1 is a protein, particularly NAD-dependent deacetylase sirtuin-1, that stimulates autophagy by preventing acetylation of proteins (via deacetylation).

In yet another embodiment, the SIRT1 activators are particularly $NAD^+$ precursors which are selected from the group consisting of nicotinamide riboside (NR), nicotinic acid (NA), nicotinamide (NAM), and/or nicotinamide derivatives such as nicotinamide mononucleotide (NMN) and N(1)-methyl nicotinamide (MNA) and pharmaceutically acceptable salts thereof.

In another preferred embodiment the SIRT1 activator is nicotinamide riboside chloride. It is represented by chemical formula $C_{11}H_{15}ClN_2O_5$ as depicted in Formula II.

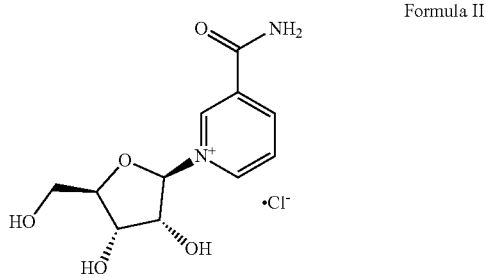 [SMILES: NC(=O)c1ccc[n+]([C@@H]2O[C@H](CO)[C@@H](O)[C@H]2O)c1 ; [Cl-]]

Formula II

SIRT1 overexpression in neurons promotes neurite outgrowth and cell survival through inhibition of the mTOR signaling.

The co-administration of SIRT1 activator preferably NR along with NBP controls mTOR activation and infarct volume through inhibition of neuron apoptosis and activation of autophagy that subsequently improve neurological function.

Precisely, the present nicotinamide precursor-NR acts as mTOR inhibitor when administrated before or after ischemic stroke that substantially improves neurologic function and decreases infarct volume by decreasing the number of neurons apoptosis and activating autophagy process. These results indicate that mTOR signaling pathway is a potential target for neuroprotection in ischemic brain treatment.

In further embodiment, the invention provides synergistic nutritional composition comprising therapeutically effective amount of SIRT1 activator along with pharmaceutically acceptable salts thereof, wherein SIRT1 activator is nicotinamide riboside chloride present in the range of 1-500 mg of total composition.

More particularly, the present invention offers synergistic effects of combined standardized celery seed extract (CSE) enriched with Dl-3-N-Butylphthalide (NBP) Nicotinamide Riboside (NR) for treating cerebral ischemia/stroke. The active moieties of the present composition are present in a therapeutically effective amount. The composition imparts significant effect to the subject in need thereof with enhanced bioavailability and efficacy.

In one embodiment, the invention provides a synergistic nutritional composition(s) for treating cerebrovascular diseases in a subject in need thereof comprising therapeutically active exogenous combination of standardized celery seed extract (CSE) enriched with Dl-3-N-Butylphthalide (NBP) and SIRT1 activator(s), wherein the standardized celery seed extract (CSE) enriched with Dl-3-N-Butylphthalide (NBP) and SIRT1 activator are present in a weight ratio of 1:0.1 to 1:5 along with pharmaceutically acceptable excipients.

In another preferred embodiment, the invention provides synergistic nutritional compositions for treating stroke conditions comprising therapeutically active exogenous combination of standardized celery seed extract (CSE) enriched with Dl-3-N-Butylphthalide (NBP) and Nicotinamide Riboside (NR) chloride present in the weight ratio of 1:0.5 to 1:5 along with pharmaceutically acceptable excipients.

The term 'standardized CSE' refers to supplements that provide a specific concentration of therapeutically effective chemical constituent called Dl-3-N-Butylphthalide (NBP).

In one more embodiment, the invention provides synergistic nutritional composition comprising combination of standardized celery seed extract (CSE) enriched with Dl-3-N-Butylphthalide (NBP) and SIRT1 activator, wherein the effective amount of standardized (CSE) enriched with (NBP) is present in the range of 30% to 50% by weight of total composition.

In further embodiment, the invention provides synergistic nutritional compositions comprising standardized celery seed extract (CSE) enriched with Dl-3-N-Butylphthalide (NBP), wherein the effective amount of Dl-3-N-Butylphthalide (NBP) is present in the range of 15% to 40% by weight of total composition.

In one more embodiment, the invention provides synergistic nutritional compositions comprising standardized celery seed extract (CSE) enriched with Dl-3-N-Butylphthalide (NBP), wherein Dl-3-N-Butylphthalide (NBP) is present in a range of 40% to 90% by weight of the total CSE.

Particularly standardized celery seed extract (CSE) is containing 40% to 90% of Dl-3-N-Butylphthalide (NBP), more particularly 80% to 90% of NBP as therapeutically active constituent.

In yet another embodiment, the invention provides synergistic nutritional composition comprising SIRT1 activators, wherein the effective amount of SIRT1 activators are present in the range of 40% to 70% by weight of the total composition.

In yet another embodiment, the invention provides synergistic nutritional composition comprising nicotinamide riboside chloride as SIRT1 activator, wherein the effective amount of nicotinamide riboside chloride is present in the range of 40% to 70% by weight of the total composition.

In another preferred embodiment, the invention provides an anti-stroke synergistic nutritional composition comprising therapeutically active exogenous combination of Dl-3-N-Butylphthalide (NBP) and Nicotinamide Riboside chloride present in the weight ratio of 1:0.2 to 1:5 along with pharmaceutically acceptable excipients.

In another embodiment the invention provides an anti-stroke synergistic nutritional composition, wherein the effective amount of Dl-3-N-Butylphthalide (NBP) is present in the range of 10% to 50% by weight of the total composition.

In another embodiment the invention provides an anti-stroke synergistic nutritional composition, wherein the effective amount of nicotinamide riboside chloride is present in the range of 40% to 80% by weight of the total composition.

In yet another embodiment, the invention provides exogenous supplementation with NAD+ and SIRT1 enhancers that afford synergistic neuroprotective effects in subject having ischemic neuronal injury induced by oxygen-glucose deprivation (OGD). Remarkably cellular NAD+ replenishment exhibits neuroprotection against ischemic injury in combination with mTOR inhibitors.

In another preferred embodiment, the instant invention provides nutritional booster composition with synergistic effect for treating cerebral ischemia, wherein the effective amount of celery extract enriched with 80-90% NBP elevates NAD level after stroke and protects against ischemia induced energy depletion, neural cell death, and eventually brain infarction. It further enhances brain capillary density, increases number of proliferating endothelial cells and improves blood flow recovery. Further NBP induced BDNF activation modulate local inflammation in ischemic brain tissues on the cellular, cytokine, and transcription factor levels; on the other side the NR inhibits mTOR signaling pathway that controls infarct volume through inhibition of neuron apoptosis and activation of autophagy that subsequently improve neurological function.

In another preferred embodiment, the present nutritional composition promotes neuroprotection particularly stroke salvage, wherein both active moieties regulate cerebral stroke concomitantly and synergistically, moreover the composition controls neuronal damage, promotes neuronal viability, activity and neurite re-growth, restores brain blood flow and thus mitigates the effects of ischemia.

In the instant invention the term 'hybrid' or 'neuroprotective therapy' or 'combination therapy' or 'concomitant therapy' denotes the characteristics or inventive feature of the instant composition, wherein the active moieties performing simultaneous function in systematic cellular pathways without any deviation or disruption, that consequently improve cerebral ischemic induced conditions.

In an additional embodiment, the present composition may comprise bioenhancer that improves the in-vivo bioavailability by ameliorating solubility and absorption of the composition.

Certain compounds of the present invention can exist in unsolvated forms as well as solvated forms, including hydrated forms. Further some compounds of the present invention can exist in multiple crystalline or amorphous forms ("polymorphs"). In general, all physical forms are of use in the method contemplated by the present invention and are intended to be within the scope of the invention. Compound or a pharmaceutically acceptable salts, hydrates, polymorphs or solvates of a compound intends the inclusive meaning of "or", in that materials meeting more than one of the stated criteria are included, e.g., a material that is both a salt and a solvate is encompassed.

Compounds of the invention can exist in particular geometric or, enatiomeric or stereoisomeric forms. The invention contemplates all such compounds, including dextrorotatory and levorotatory-isomers, rectus and sinister configuration. All such isomers, as well as racemic mixtures thereof, are intended to be included in this invention.

In another embodiment, the invention provides synergistic nutritional composition which is useful for treating cerebrovascular diseases including but not limited to stroke, carotid stenosis, vertebral stenosis, intracranial stenosis, aneurysms, vascular malformations, cerebral ischemia, brain ischemia, cerebral infarction, cerebral edema, cerebral stroke, postischemic stroke, acute ischemic stroke, hemorrhagic stroke, transient ischemic attacks, hypoxic brain injury, cerebral hypoxia, global hypoxia-ischemia, brain trauma, subarachnoid haemorrhage, intracerebral haemorrhage, nervous system trauma or conditions related to neuroplasticity, neuroinflammation, brain attack, brain damage, acute cryptogenic stroke and like thereof.

As used herein, the term "therapeutically effective amount" is intended to mean the amount of active compounds of the present invention to be effective for treating cerebral ischemia induced diseases or conditions through synergistic effect.

The therapeutically effective amount of such actives may vary depending upon the subject and disease condition being treated, the weight and age of the subject, the severity of the disease condition, the manner of administration and the like, which can readily be determined by one of ordinary skill in the art.

Thus, a "therapeutically effective amount" is an amount that reduces the risk, potential, possibility or occurrence of a disease or disorder, or provides advanced alleviation, mitigation, and/or reduction or restoration of at least one indicator/biomarker (e.g., blood or serum CRP level), and/or minimize at least one clinical symptom of cerebral ischemia/stroke.

The "subject in need thereof" pertains to subject preferably mammal, more preferably human suffering with cerebrovascular diseases like stroke or ischemia, brain damage or injury or stroke survivors or subject with high prevalence or incidence of stroke risk factors.

In the context of the present invention, the terms "treatment" and the like refer to alleviate, mitigate, prophylaxis, attenuate, manage, regulate, modulate, control, minimize, lessen, decrease, down regulate, up regulate, moderate, prevent, inhibit, stabilize, ameliorate or cure, heal the stroke inducing parameters.

Notably, the instant synergistic composition is non-hazardous, non-toxic and safe for human consumption without any side effects, therefore the instant composition can also be used under preventive therapy in healthy subjects.

As used herein, the term "pharmaceutically acceptable carriers, diluents or excipients" is intended to mean, without limitation, any adjuvant, carrier, excipient, sweetening agent, diluents, preservative, dye/colorant, flavor enhancer, surfactant, wetting agent, dispersing agent, suspending agent, stabilizer, isotonic agent, solvent, emulsifier, or encapsulating agent, encapsulating polymeric delivery systems or polyethylene glycol matrix, which is acceptable for use in the subject, preferably humans. Excipients may also include, for example: anti adherents, antioxidants, binders, coatings, compression aids, disintegrants, dyes (colors), emollients, emulsifiers, fillers (diluents), film formers or coatings, fragrances, glidants (flow enhancers), lubricants, preservatives, sorbents, suspending or dispersing agents, sweeteners, surfactant, anticaking agent, food additives, or waters of hydration, salts.

In another embodiment, the invention relates to synergistic composition, which can be prepared in a manner well known in the pharmaceutical art, and can be administered by a variety of routes, depending upon whether local or systemic treatment is desired and upon the area to be treated. The preferable route of administration includes but not limited to sublingual, rectal, topical, parenteral, nasal or oral.

Therapeutic (prescription) supplements are generally administered by the oral or parenteral or nasal routes for curing stroke conditions. The therapeutic administration of materials of the present invention may be in conjunction with other therapies.

Further, the instant synergistic nutritional composition can be administered to subject in a form suitable for oral use, such as a tablet, capsule (in the form of delayed release, extended release, sustained release, enteric coated release), hard gelatin capsules, soft gelatin capsules in an oily vehicle, granulate for sublingual use, effervescent tablets, aqueous or oily solution, suspension or emulsion, encapsulate, matrix, coat, beadlets, nanoparticles, caplet, granule, particulate, agglomerate, spansule, chewable tablet, lozenge, troche, solution, suspension, rapidly dissolving film, elixir, gel, as tablets, pellets, granules, capsules, lozenges, aqueous or oily solutions, suspensions, emulsions, sprays or reconstituted dry powdered form with a liquid medium or syrup. Further the composition can be formulated for parenteral use including intravenous, subcutaneous, intramuscular, intravascular, infusion, intraperitoneal, intracerebral, intracerebroventricular, or intradermal.

Further the instant synergistic composition can be made useful for nasal administration through ion liquid spray device, nasal spray, intranasal spray device, nanonasal spray, saline spray and like thereof.

In another embodiment, the oral administration of effective dose of the present synergistic nutritional composition comprising exogenous blend of NBP and NR in weight ratio of 1:1 to 1:3 that significantly improves stroke conditions.

In some embodiment, the pharmaceutically acceptable carriers, diluents or excipients are selected from the group consisting of adjuvant, carrier, excipient, glidant, sweetening agent, diluent, preservative, dye/colorant, flavor enhancer, surfactant, wetting agent, dispersing agent, suspending agent, stabilizer, isotonic agent, solvent, emulsifier, or encapsulating agent, such as a liposome, cyclodextrins, encapsulating polymeric delivery systems or polyethylene glycol matrix, which is acceptable for use in the subject, preferably humans. Excipients may also include, for example: anti adherents, antioxidants, binders, coatings, compression aids, disintegrants, dyes (colors), emollients, emulsifiers, fillers (diluents), film formers or coatings, fragrances, glidants (flow enhancers), lubricants, preservatives, sorbents, suspending or dispersing agents, sweeteners, surfactant, anticaking agent, food additives, or waters of hydration.

In some embodiment of the invention, the diluents are selected from starches, hydrolyzed starches, and partially pregelatinized starches, anhydrous lactose, cellulose powder, lactose monohydrate, and sugar alcohols such as sorbitol, xylitol and mannitol, silicified microcrystalline cellulose, ammonium alginate, calcium carbonate, calcium lactate, dibasic calcium phosphate (anhydrous/dibasic dehydrate/tribasic), calcium silicate, calcium sulfate, cellulose acetate, corn starch, pregelatinized starch, dextrin, β-cyclodextrin, dextrates, dextrose, erythritol, ethyl cellulose, fructose, fumaric acid, glyceryl palmitostearate, magnesium carbonate, magnesium oxide, maltodextrin, maltose, medium-chain triglycerides, polydextrose, polymethacrylates, sodium alginate, sodium chloride, sterilizable maize, sucrose, sugar spheres, talc, trehalose, xylitol, vehicles like petrolatum, dimethyl sulfoxide and mineral oil or the like.

In some embodiment of the invention, the amount of diluent in the composition/formulation is present in the range of 1% to 30% by wt. of the total composition/formulation.

In some embodiment, the binder is selected from disaccharides such as sucrose, lactose, polysaccharides and their derivatives like starches, cellulose or modified cellulose such as microcrystalline cellulose and cellulose ethers such as hydroxypropyl cellulose (HPC); hydroxypropyl methyl cellulose (HPMC); sugar alcohols such as xylitol, sorbitol or mannitol; protein like gelatin; synthetic polymers such as polyvinylpyrrolidone (PVP), polyethylene glycol (PEG), starch, acacia, agar, alginic acid, calcium carbonate, calcium lactate, carbomers, carboxymethylcellulose sodium, carrageenan, cellulose acetate phthalate, chitosan, copovidone, corn starch, pregelatinized starch, cottonseed oil, dextrates, dextrin, dextrose, ethyl cellulose, guar gum, hydrogenated vegetable oil, mineral oil, hydroxyethyl cellulose, hydroxymethyl cellulose hydroxyl ethylmethyl cellulose, hydroxypropyl cellulose, inulin, cellulose, methyl cellulose, polyvinylpyrrolidone and polyethylene glycol, lactose, liquid glucose, hypromellose, magnesium aluminum silicate, maltodextrin, maltose, methyl-cellulose, microcrystalline cellulose, pectin, poloxamer, polydextrose, polymethacrylates, povidone, sodium alginate, stearic acid, sucrose, sunflower oil, various animal vegetable oils, and white soft paraffin, paraffin, flavorants, colourants and wax.

In some embodiment of the invention, the amount of binder in the composition/formulation is present in the range of 0.1% to 30% by wt. of the composition/formulation.

In further embodiment, the lubricant is selected from magnesium stearate, zinc stearate, calcium stearate, glycerin monostearate, glyceryl behenate, glyceryl palmitostearate, hydrogenated castor oil, hydrogenated vegetable oil, light mineral oil, magnesium lauryl sulfate, medium-chain triglycerides, mineral oil, myristic acid, palmitic acid, poloxamer, polyethylene glycol, sodium benzoate, sodium chloride, sodium lauryl sulfate, sodium stearyl fumarate, stearic acid, talc, potassium, or sodium benzoate or the like.

In some embodiment of the invention, the amount of lubricant in the composition/formulation is present in the range of 0.1% by wt. to 5.0% by wt. of the total composition/formulation.

In another embodiment, the solubilizing agent is selected from polysorbate 80, sodium lauryl sulfate, anionic emulsifying wax, nonionic emulsifying wax, glyceryl monooleate, phospholipids, polyoxyethylene alkyl ethers, polyoxyethylene castor oil derivatives, polyoxyethylene sorbitan fatty acid esters, polyoxyethylene stearates, polyoxylglycerides, sorbitan esters, triethyl citrate, vitamin E, polyethylene glycol succinate, microcrystalline cellulose, carboxymethylcellulose sodium, diethanolamine, ethylene glycol palmitostearate, glycerin monostearate, hypromellose, hypromellose, acetate succinate, lecithin, polyethylene alkyl ethers, aluminum oxide, poly(methylvinyl ether/maleic anhydride), calcium carbonate, crospovidone, cyclodextrins, fructose, hydroxypropyl betadex, oleyl alcohol, povidone, benzalkonium chloride, benzethonium chloride, benzyl alcohol, benzyl benzoate, cetylpyridinium chloride, inulin, meglumine, poloxamer, pyrrolidone, sodium bicarbonate, starch, stearic acid, sulfobutylether beta cyclodextrin, tricaprylin, triolein, docusate sodium, glycine, alcohol, self-emulsifying glyceryl monooleate, cationic benzethonium chloride, cetrimide, xanthan gum, lauric acid, myristyl alcohol, butylparaben, ethylparaben, methylparaben, propylparaben, sorbic acid or the like.

In some embodiment of the invention, the amount of solubilizing agent or surfactant in the composition/formulation of the present invention ranges from 0.1% to 10%, preferably 0.1% to 5.0% by wt. of the composition/formulation.

In some embodiment, the glidant is selected from colloidal silicon dioxide, magnesium stearate, fumed silica (colloidal silicon dioxide), starch, talc, calcium phosphate tribasic, cellulose powdered, hydrophobic colloidal silica, magnesium oxide, zinc stearate, magnesium silicate, magnesium trisilicate, silicon dioxide or the like.

In some embodiment of the invention, the amount of glidant present in the composition/formulation ranges from 0.1% by wt. to 5.0% by wt. of the total composition/formulation.

In some embodiment of the inventions, the stabilizers are selected from the group consisting of alginate, agar, carrageen, gelatin, guar gum, gum arabic, locust bean gum, pectin, starch, xanthan gum, trehalose and likewise.

In some embodiment of the invention, the amount of stabilizers in the composition/formulation ranges from 0.1% by wt. to 8.0% by wt. of the total composition/formulation.

In some embodiment, the solvent is selected from water, alcohol, isopropyl alcohol, propylene glycol, mineral oil, benzyl alcohol, benzyl benzoate, flavored glycol, carbon dioxide, castor oil, corn oil (maize), cottonseed oil, dimethyl ether, albumin, dimethylacetamide, ethyl acetate, ethyl lactate, medium-chain triglycerides, methyl lactate, olive oil, peanut oil, polyethylene glycol, polyoxyl, castor oil, propylene carbonate, pyrrolidone, safflower oil, sesame oil, soybean oil, sunflower oil, water-miscible solvents, organic polar or non-polar solvents or mixtures thereof.

In some embodiment of the invention, the amount of solvent in the composition/formulation is used in a quantity sufficient to 100% by wt. of the composition/formulation.

The additional additives include polymer, a plasticizer, a sweetener, and a powdered flavor, preservative, colorant, surfactant and other excipients. The powdered flavor composition includes a flavorant associated with a solid carrier, coating materials are used, for example synthetic polymers, shellac, corn protein (zein) or other polysaccharides, gelatin, fatty acids, waxes, shellac, plastics, and plant fibers and like thereof.

In some embodiment of the invention, the additives are used in the range of 1 to 20% w/w of unit dose.

In another embodiment, the invention provides synergistic nutritional composition comprising exogenous blend of standardized celery seed extract (CSE) enriched with Dl-3-N-Butylphthalide (NBP) and Nicotinamide Riboside (NR) along with pharmaceutical excipients, wherein pharmaceutical excipients are a diluent present in the range of 1 to 30%; a binder present in the range of 0.1 to 25%; a lubricant present in the range of 0.1 to 5.0%; a glidant present in the range of 0.1 to 5.0%; an additive present in the range of 1 to 10%; a surfactant present in the range of 0.1 to 5.0%; a stabilizer present in the range of 0.1 to 5.0% by weight of total composition.

In another embodiment, the invention provides synergistic nutritional composition comprising exogenous blend of Dl-3-N-Butylphthalide (NBP) and Nicotinamide Riboside (NR) along with pharmaceutical excipients, wherein pharmaceutical excipients are diluent present in the range of 1 to 25%; binder present in the range of 0.1 to 20%; lubricant present in the range of 0.1 to 5.0%; glidant present in the range of 0.1 to 3.0%; additive present in the range of 1 to 5%; surfactant present in the range of 0.1 to 3.0%; stabilizer present in the range of 0.1 to 5.0% by weight of total composition.

Advantageously, the instant synergistic nutritional composition is non-hazardous, non-toxic and safe for human consumption without any severe side effects, therefore the instant composition can also be used under preventive therapy in healthy subjects.

In a preferred embodiment, the present medicinal composition/formulation is formulated for oral administration. Specifically, the solid medicinal compositions, for example, can be in the form of tablets, capsules, pills, hard capsules filled with liquids or solids, soft capsules, sachets, powders, granules, suspensions, solutions or modified release formulations. Formulations of the present invention suitable for oral administration can be presented as discrete units such as capsules (e.g., soft-gel capsules, hard-gel capsule), cachets or tablets each containing a predetermined amount of the active ingredient; as a powder or granules; as a solution or a suspension in an aqueous liquid or a non-aqueous liquid, syrup; or as an oil-in-water liquid emulsion or a water-in-oil liquid emulsion.

Further the present composition can be formulated in the form of age-appropriate pediatric oral dosage forms such as syrup, minitablets, chewable formulations, or dispersible films or dispersible tablets.

The magnitude of a prophylactic or therapeutic dose typically varies with the nature and severity of the condition to be treated and the route of administration. The dose, and perhaps the dose frequency, will also vary according to the age, body weight and response of the individual patient. In general, the total daily dose (in single or divided doses) ranges from about 1 mg per day to about 5000 mg per day, preferably about 50 mg per day to about 1500 mg per day.

In some embodiment, the total daily dose can be administered orally in the range of about 5 mg to about 2000 mg per day, and preferably about 10 mg to about 1000 mg per day.

The synergistic nutritional compositions, comprising specific combination of standardized celery seed extract (CSE) enriched with Dl-3-N-Butylphthalide (NBP) and Nicotinamide Riboside (NR) and salts thereof along with pharmaceutically acceptable excipients or carriers, wherein the effective unit dose for oral administration is formulated in the range of 50 to 500 mg.

It is further recommended that children, patients over 60 years old, initially receive low doses and that the dosage be titrated based on individual physiological responses and/or pharmacokinetics. It can be necessary to use dosages outside these ranges in some cases, as will be apparent to those in the art.

Further, it is noted that the dietician or nutritionist or certified physician knows how and when to interrupt, adjust or terminate therapy in conjunction with an individual patient's response.

The use of any and all examples, or exemplary language (e.g., "such as") provided herein, is intended merely to better illuminate the invention and does not pose a limitation on the scope of the invention unless otherwise claimed.

While in the foregoing specification this invention has been described in relation to certain embodiments thereof, and many details have been put forth for the purpose of illustration, it will be apparent to those skilled in the art that the invention is susceptible to additional embodiments and that certain of the details described herein can be varied considerably without departing from the basic principles of the invention.

The invention may be further illustrated by the following examples, which are for illustrative purposes only and should not be construed as limiting the scope of the invention in anyway.

The present invention is not to be limited in terms of the particular embodiments described in this application, which are intended as single illustrations of individual aspects of the invention. Functionally equivalent compositions and treatments within the scope of the invention, in addition to those enumerated herein, will be apparent to those skilled in the art from the foregoing description and examples. Such modifications and variations are intended to fall within the scope of the appended claims. The contents of each reference, patent and patent application cited in this application is hereby incorporated by reference in its entirety.

EXAMPLES

Example-1 i. Composition 1: Synergistic Blend

| Ingredient | w/w % |
|---|---|
| Standardized celery seed extract (CSE) enriched with Dl-3-N-Butylphthalide (NBP) | 30% to 50% |
| SIRT1 activators | 40% to 70% | ii. Composition 2: Synergistic Blend

| Ingredient | w/w % |
|---|---|
| Standardized celery seed extract (CSE) enriched with | 30% to 50% |

-continued

| Ingredient | w/w % |
|---|---|
| Dl-3-N-Butylphthalide (NBP) | |
| Nicotinamide riboside chloride | 40% to 70% | iii. Composition 3: Synergistic Blend

| Ingredient | w/w % |
|---|---|
| Dl-3-N-Butylphthalide (NBP) | 15% to 40% |
| Nicotinamide riboside chloride | 40% to 70% | iv. Composition 4: Tablet/Capsule

| Ingredient | w/w % unit dose |
|---|---|
| Standardized celery seed extract (CSE) enriched with Dl-3-N-Butylphthalide (NBP) | 40 ± 5% |
| Nicotinamide Riboside (NR) | 55 ± 5% |
| Excipient | 5-10% |
| Average Wt | 100% | v. Composition 5: Tablet/Capsule

| Ingredient | w/w % unit dose |
|---|---|
| Standardized celery seed extract (CSE) enriched with Dl-3-N-Butylphthalide (NBP) | 37.5% |
| Nicotinamide Riboside (NR) | 50% |
| Diluents | 1-10% |
| Binders | 0.5-5% |
| Glidants | 0.5-5% |
| Lubricants | 0.5-5% |
| Stabilizers | 0.1-10% |
| Additives | 1-10% |
| Solvents | QS | vi. Composition 6: Tablet/Capsule

| Ingredient | w/w % unit dose |
|---|---|
| Standardized celery seed extract (CSE) enriched with Dl-3-N-Butylphthalide (NBP) | 33% |
| Nicotinamide Riboside (NR) | 50% |
| Diluent | 1-20% |
| Binder | 0.5-5% |
| Glidant | 0.5-5% |
| Lubricants | 0.5-5% |
| Additives | 1-10% |
| Solvent | QS | vii. Composition 7: Tablet/Capsule

| Ingredient | mg per unit dose |
|---|---|
| Standardized celery seed extract (CSE) enriched with Dl-3-N-Butylphthalide (NBP) | 75 |
| Nicotinamide Riboside Chloride | 100 |
| Microcrystalline Cellulose | 1-20 |
| Silicon dioxide | 1-10 |
| Hydroxypropyl Methylcellulose | 1-10 |
| Zinc Stearate | 1-10 |
| PVP K-30 | 5-10 |
| Talc | 1-10 |

-continued

| Ingredient | mg per unit dose |
|---|---|
| Polysorbate 80 | 1-10 |
| Mannitol | 1-20 |
| Propylene Glycol | QS |
| Water | QS |
| Average weight | 200-250 mg | viii. Composition 8: Tablet/Capsule

| Ingredient | mg per unit dose |
|---|---|
| Standardized celery seed extract (CSE) enriched with Dl-3-N-Butylphthalide (NBP) | 100 |
| Nicotinamide Riboside (NR) | 150 |
| Sodium ascorbate | 1-10 |
| Microcrystalline Cellulose | 2-20 |
| Silicon dioxide | 1-10 |
| Hydroxypropyl Methylcellulose | 2-10 |
| Magnesium Stearate | 2-10 |
| PVP K-30 | 1-10 |
| Talc | 1-10 |
| Polysorbate 80 | 2-20 |
| Mannitol | 2-20 |
| Alcohol | QS |
| Water | QS |
| Average weight | 300-350 mg | ix. Composition 9: Tablet/Capsule

| Ingredient | mg per unit dose |
|---|---|
| Standardized celery seed extract (CSE) enriched with Dl-3-N-Butylphthalide (NBP) | 50 |
| Nicotinamide Riboside (NR) | 62.5 |
| Sodium ascorbate | 1-10 |
| Microcrystalline Cellulose | 2-20 |
| Silicon dioxide | 5-15 |
| Hydroxypropyl Methylcellulose | 2-10 |
| Magnesium Stearate | 2-10 |
| PVP K-30 | 5-10 |
| Talc | 1-10 |
| Polysorbate 80 | 5-20 |
| Mannitol | 5-20 |
| Methylene Chloride | QS |
| Water | QS |
| Average weight | 150-200 mg |

Example 2: Animal Study

"Neuroprotective Effect of Test Product against Global Ischemia Reperfusion Induced Brain Injury (Cerebral Infarction) in Wistar Rats"

Test System and Animal Husbandry
Species: Rats
Strain: Wistar
Sex: Male
No. of animals: 36 Animals (n=6 per group)
Body weight: 200-220 gm
CPCSEA Registration Number-1803/PO/RcBi/S/2015/CPCSEA
Animal House Conditions
Lighting: 12/12 hour light-dark cycle
Temperature: 22±3° C.
Relative Humidity: 30 to 70%
Animals had continuous access to fresh, potable, uncontaminated drinking water.
Feed: Normal chow diet [PURINA 5L79 from PMI Nutritional, USA]

Group, Designation and Dose Levels:

TABLE 1

Animal grouping and treatment details

| Groups | Group Description | Treatment Description | No. of animals |
|---|---|---|---|
| Group 1 | Normal Control (Without Exposure of Ischemia Reperfusion) | 0.5% (Carboxymethyl cellulose - CMC) | 06 |
| Group 2 | Ischemia Reperfusion (I/R) Control (Exposure of Ischemia Reperfusion) | 0.5% CMC | 06 |
| Group 3 | Standard (Cerebroprotein hydrolysate (Tablet) + Exposure of Ischemia Reperfusion) | 9.3 mg/kg | 06 |
| Group 4 | 3-N-butylpthalide (NBP) + Exposure of Ischemia Reperfusion | 49.6 mg/kg | 06 |
| Group 5 | Nicotinamide Riboside chloride (NR) + Exposure of Ischemia Reperfusion | 31 mg/kg | 06 |
| Group 6 | (3-N-butylpthalide (NBP) + Nicotinamide Riboside chloride (NR)) + Exposure of Ischemia Reperfusion | 49.6 mg/kg + 31 mg/kg | 06 |

Test Items, Vehicle and Formulation Details

Test item: G4, G5, G6

Dose: G4-49.6 mg/kg; G5-31 mg/kg; G6-49.6 mg/kg+31 mg/kg

Route: Oral route (p.o)

Frequency: Daily

Experimental Procedure:

Animals were divided into ten groups; each group consisted of 6 animals. Group 1 was served as a Normal control and treated with vehicle 0.5% CMC; Group 2 was served as Ischemia Reperfusion control and treated with vehicle 0.5% CMC, whereas Group 3 was treated with standard product (Cerebroprotein hydrolysate). Group 4 and Group 5 received test sample 3-N-butylpthalide (NBP) and test sample Nicotinamide Riboside chloride (NR) respectively. Group 6 received test sample 3-N-butylpthalide (NBP) and test sample Nicotinamide Riboside chloride (NR) in combination.

Treatment was given orally for 10 days. Test substances NBP (49.6 mg/kg), NR (31 mg/kg), NBP+NR (49.6 mg/kg+ 31 mg/kg), were administrated orally for 10 days. At the end of the experimental period, blood was collected for biochemical analyses and animals were sacrificed for histological analysis.

On 7th day, all the experimental animals, excluding Group 1, were exposed to ischemia followed by 72 hrs reperfusion along with treatment. After 72 hrs of reperfusion, the animals were euthanized by isoflurane until breathing stops. The rats were decapitated immediately and their brains were extraction for biochemistry and TTC staining.

The results of the test substances effectively prevent neuron cells from death caused by cerebral ischemia or reperfusion and protect from brain damage.

i. Induction of Cerebral Infarction:

Induction of Global cerebral ischemia/reperfusion was carried out using the standard method. The rats were anaesthetized with an i.p. co-injection of ketamine (85 mg/kg) and xylazine (15 mg/kg) and a midline ventral incision was made in the throat. Right and left common carotid arteries were located and free from surrounding tissue and vagus nerve. A cotton thread was passed below each artery. Global cerebral ischemia was induced by occluding the carotid arteries with a knot. After 30 mins of global cerebral ischemia, the cotton thread was removed with the help of two knot releasers to allow the reperfusion of blood through carotid arteries for 72 hrs. All surgical procedures were carried out under aseptic and sterile condition.

ii. Tetrazolium Chloride Staining (TTC Staining):

The rats were anesthetized and received cardiac perfusion with 100 ml cold saline. The brains were carefully removed. The brains were frozen at −20° C. for 20 min, and then cut from the anterior pole into five coronal slices of 2 mm thickness. The slices were stained with 2% 2, 3, 5 -triphenyltetrazolium chloride solution in the dark at 37° C. in an incubator for 30 min, and turned over every 5 min. A 10% buffered-formalin solution was used for fixation (24 h) prior to imaging. The normal brain tissue was stained red, whereas the ischemic area remained unstained.

iii. Statistical Analysis

The values were expressed in Mean±sem. The significance of in vivo data was analyzed by one way Anova followed by Dunnet test. P<0.05 was considered as significant.

Results

TABLE 2

Effect of test substances on Rat body weight
Body Weight (gm)

| Group | Treatment | Basal | Week 01 |
|---|---|---|---|
| Group 1 | Normal Control (0.5% CMC) | 214.67 ± 0.76 | 225.33 ± 0.71 |
| Group 2 | Positive Control (0.5% CMC) | 214.50 ± 0.92 | 225.00 ± 0.68 |
| Group 3 | Standard (9.3 mg/kg) | 213.83 ± 0.95 | 224.67 ± 0.84 |
| Group 4 | 3-N-butylpthalide (NBP) (49.6 mg/kg) | 214.50 ± 1.12 | 224.50 ± 0.76 |
| Group 5 | Nicotinamide Riboside chloride (NR) (31 mg/kg) | 215.00 ± 1.46 | 224.83 ± 1.08 |
| Group 6 | 3-N-butylpthalide (NBP) (49.6 mg/kg) + Nicotinamide Riboside chloride (NR) (31 mg/kg) | 214.67 ± 0.88 | 224.50 ± 0.76 |

Values were expressed as mean ± SEM (n = 6), Statistical significance are compared between Ischemic Reperfusion control (Group 2) versus other treatment groups (G1, G3, G4, G5, G6) (*P Value < 0.05; P Value < 0.001; *P Value < 0.0001).

TABLE 3

Effect of test substances on Rat Feed Consumption
Feed Consumption (gm)

| Group | Treatment | Week 01 |
|---|---|---|
| Group 1 | Normal Control (0.5% CMC) | 101.71 ± 1.43 |
| Group 2 | Positive Control (0.5% CMC) | 101.29 ± 1.27 |
| Group 3 | Standard (9.3 mg/kg) | 101.14 ± 0.91 |
| Group 4 | 3-N-butylpthalide (NBP) (49.6 mg/kg) | 99.57 ± 1.00 |
| Group 5 | Nicotinamide Riboside chloride (NR) (31 mg/kg) | 99.71 ± 1.04 |
| Group 6 | 3-N-butylpthalide (NBP) (49.6 mg/kg) + Nicotinamide Riboside chloride (NR) (31 mg/kg) | 98.86 ± 0.83 |

TABLE 4

Effect of test substances on Rat TNF alpha Level
TNF alpha Level (pg/ml)

| Group | Treatment | TNF alpha |
|---|---|---|
| Group 1 | Normal Control (0.5% CMC) | 71.17 ± 3.48 |
| Group 2 | Positive Control (0.5% CMC) | 172.17 ± 6.35 |
| Group 3 | Std (9.3 mg/kg) | 109.00 ± 3.02*** |

TABLE 4-continued

Effect of test substances on Rat TNF alpha Level
TNF alpha Level (pg/ml)

| Group | Treatment | TNF alpha |
|---|---|---|
| Group 4 | 3-N-butylpthalide (NBP) (49.6 mg/kg) | 132.00 ± 2.34*** |
| Group 5 | Nicotinamide Riboside chloride (NR) (31 mg/kg) | 160.33 ± 4.79* |
| Group 6 | 3-N-butylpthalide (NBP) (49.6 mg/kg) + Nicotinamide Riboside chloride (NR) (31 mg/kg) | 128.67 ± 0.84*** |

Values were expressed as mean ± SEM (n = 6), Statistical significance are compared between Ischemic Reperfusion control (Group 2) versus other treatment groups (G1, G3, G4, G5, G6) (*P Value < 0.05; P Value < 0.001; *P Value < 0.0001).

TABLE 5

Effect of test substances on Rat Interleukin - 6 Levels
Interleukin - 6 Levels (pg/ml)

| Group | Treatment | Interleukin - 6 |
|---|---|---|
| Group 1 | Normal Control (0.5% CMC) | 41.67 ± 1.37 |
| Group 2 | Positive Control (0.5% CMC) | 121.83 ± 1.65 |
| Group 3 | Standard (9.3 mg/kg) | 67.00 ± 1.21*** |
| Group 4 | 3-N-butylpthalide (NBP) (49.6 mg/kg) | 85.39 ± 0.62*** |
| Group 5 | Nicotinamide Riboside chloride (NR) (31 mg/kg) | 109.56 ± 0.27*** |
| Group 6 | 3-N-butylpthalide (NBP) (49.6 mg/kg) + Nicotinamide Riboside chloride (NR) (31 mg/kg) | 81.44 ± 0.69*** |

Values were expressed as mean ± SEM (n = 6), Statistical significance are compared between Ischemic Reperfusion control (Group 2) versus other treatment groups (G1, G3, G4, G5, G6) (*P Value < 0.05; P Value < 0.001; *P Value < 0.0001).

DISCUSSION

Cerebral ischemia/stroke causes dizziness, double vision, difficulty in speaking or slurred speech, loss of body coordination and sometimes paralysis, while untreated will result in unconsciousness, permanent damage to the brain or death.

The present investigation demonstrated the neuroprotective activity of test substances against Global Ischemia Reperfusion Induced Brain Injury (Cerebral Infarction) in Wistar Rats. There was not showing any significant changes on Body weight in all the groups observed when compared with Ischemia Reperfusion Control group (G2) (Table 2).

Table 3 represents the Feed intake of rats was not showing any significant changes observed in all the groups when compared with Ischemia Reperfusion Control group (G2).

Table 4 & FIG. 1 represent the TNF alpha levels showing significant decrease in the test substances treated group when compared with Ischemia Reperfusion Control group (G2).

Figure 2:
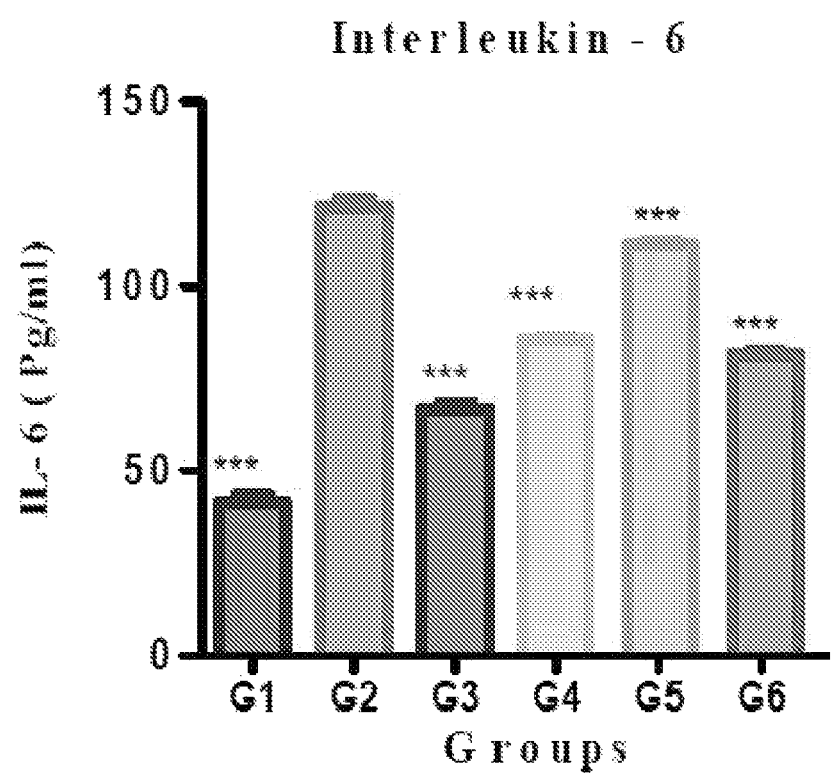
FIG. 2 illustrates the effect of test substances on Rat Interleukin-6 (IL-6) levels.
Figure 3:
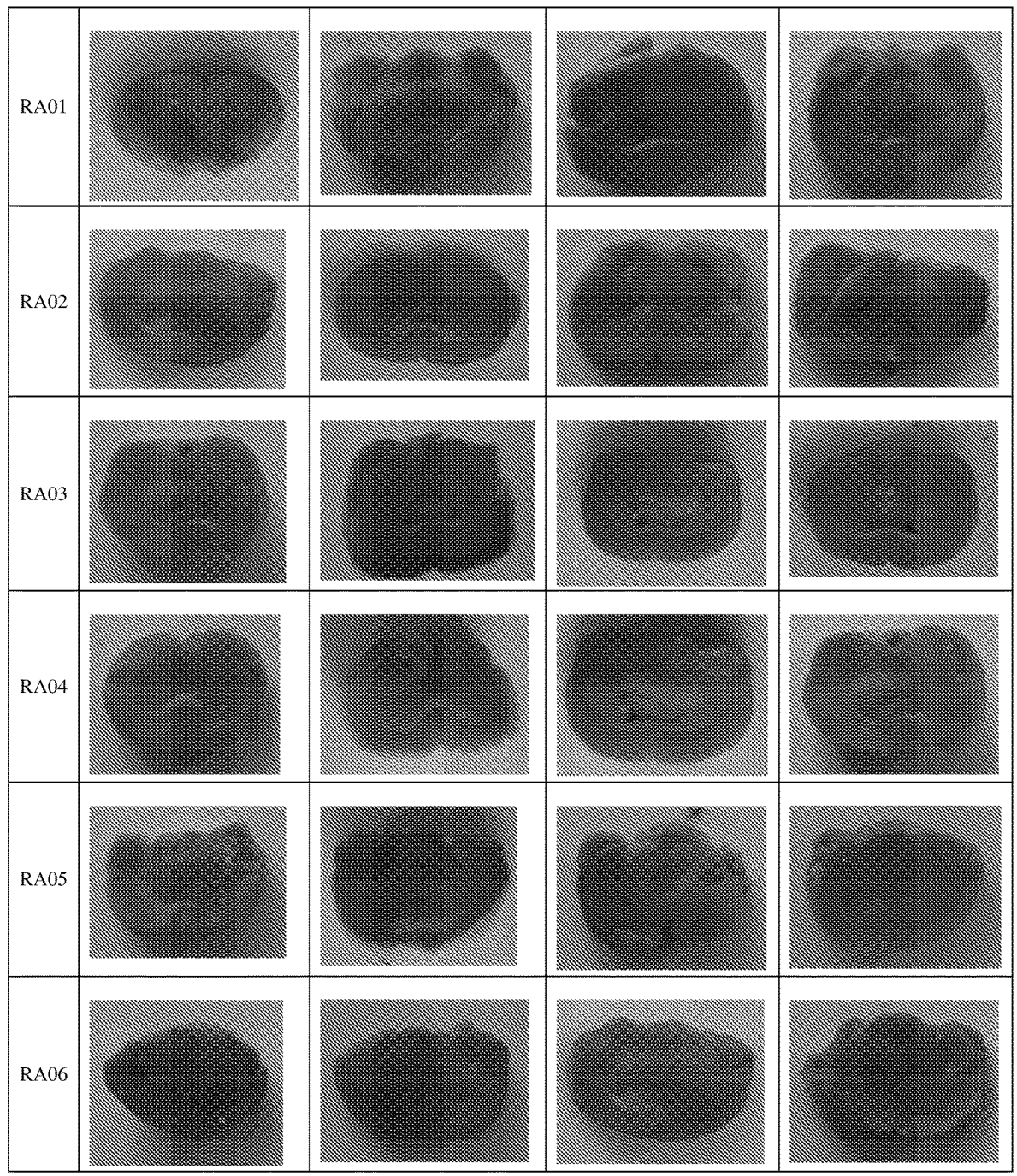
FIG. 3 illustrates the effect of test substances on Rat TTC staining—Group 1- Normal Control [RA-01 to RA-06 represent Rat model]
Figure 4:
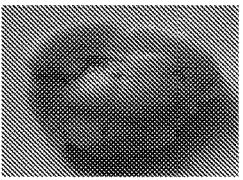
FIG. 4 illustrates the effect of test substances on Rat TTC staining—Group 2- Positive Control.
Figure 4:
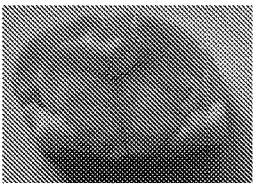
Figure 4:
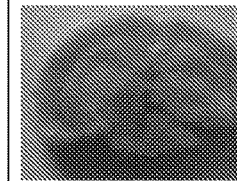
Figure 4:
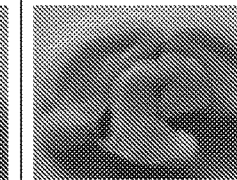
Figure 4:
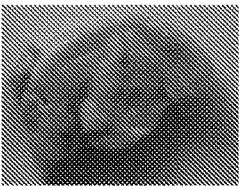
Figure 4:
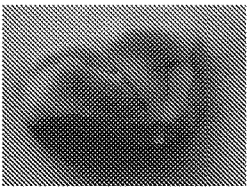
Figure 4:
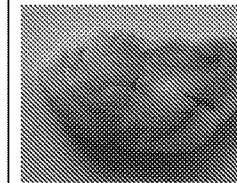
Figure 4:
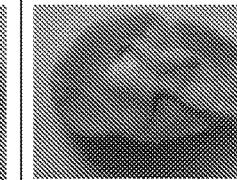
Figure 4:
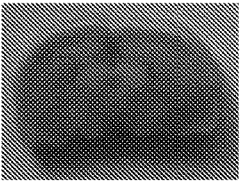
Figure 4:
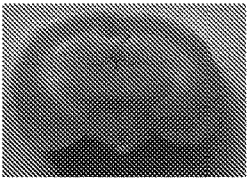
Figure 4:
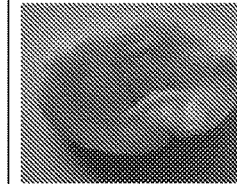
Figure 4:
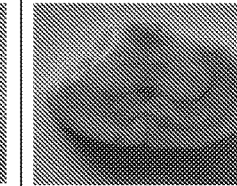
Figure 4:
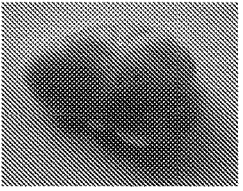
Figure 4:
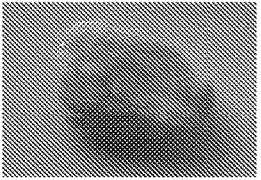
Figure 4:
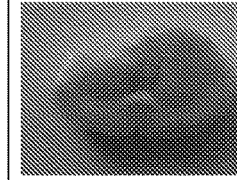
Figure 4:
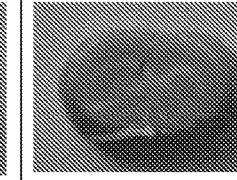
Figure 4:
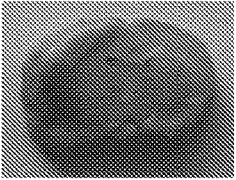
Figure 4:
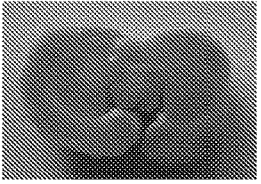
Figure 4:
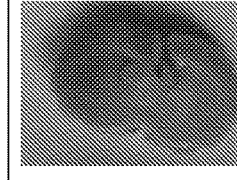
Figure 4:
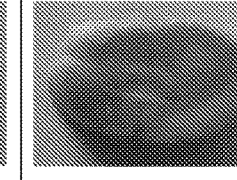
Figure 4:
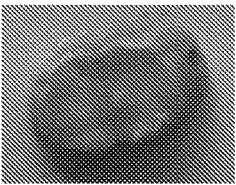
Figure 4:
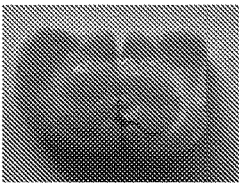
Figure 4:
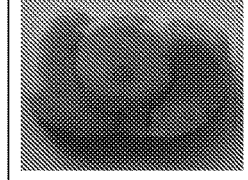
Figure 4:
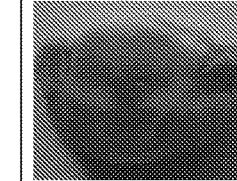

Significant decrease is seen in Interleukin −6 levels in the test substances treated group when compared with Ischemia Reperfusion Control group (G2) (Table 5 & FIG. 2).

Figure 5:
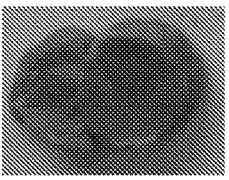
FIG. 5 illustrates the effect of test substances on Rat TTC staining—Group 3- Standard Cerebroprotein hydrolysate (Tablet)
Figure 5:
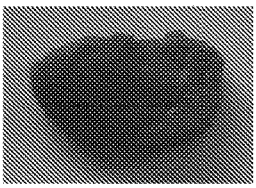
Figure 5:
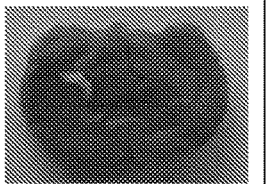
Figure 5:
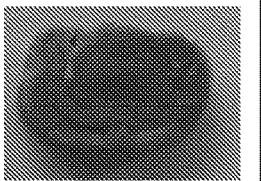
Figure 5:
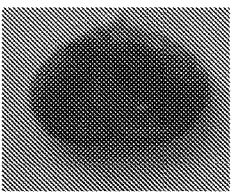
Figure 5:
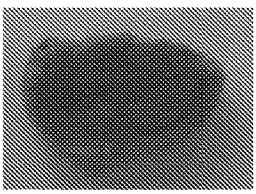
Figure 5:
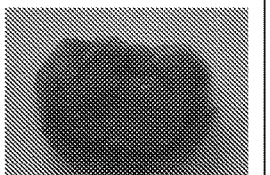
Figure 5:
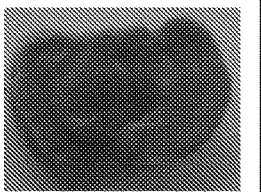
Figure 5:
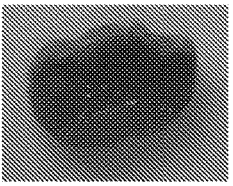
Figure 5:
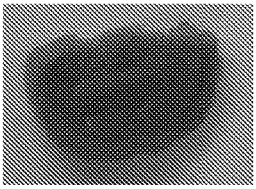
Figure 5:
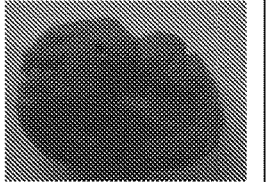
Figure 5:
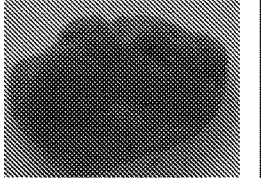
Figure 5:
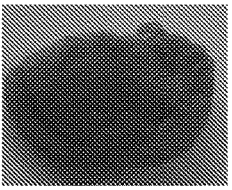
Figure 5:
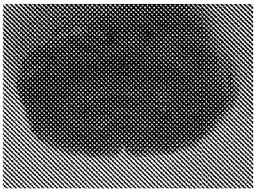
Figure 5:
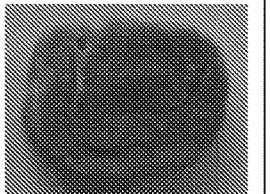
Figure 5:
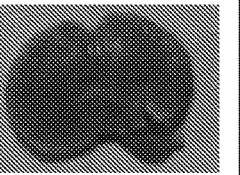
Figure 5:
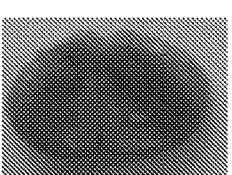
Figure 5:
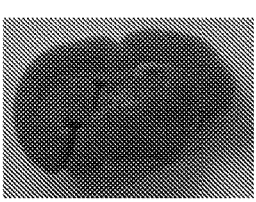
Figure 5:
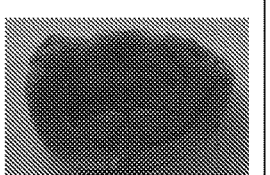
Figure 5:
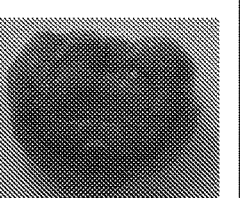
Figure 5:
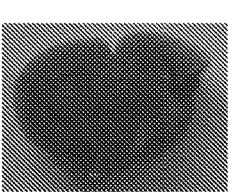
Figure 5:
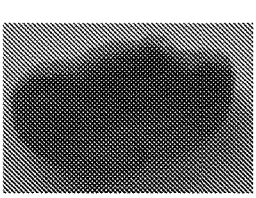
Figure 5:
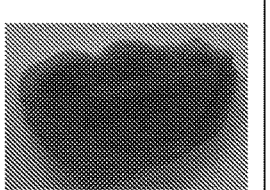
Figure 5:
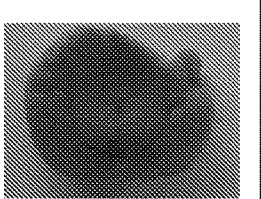
Figure 6:
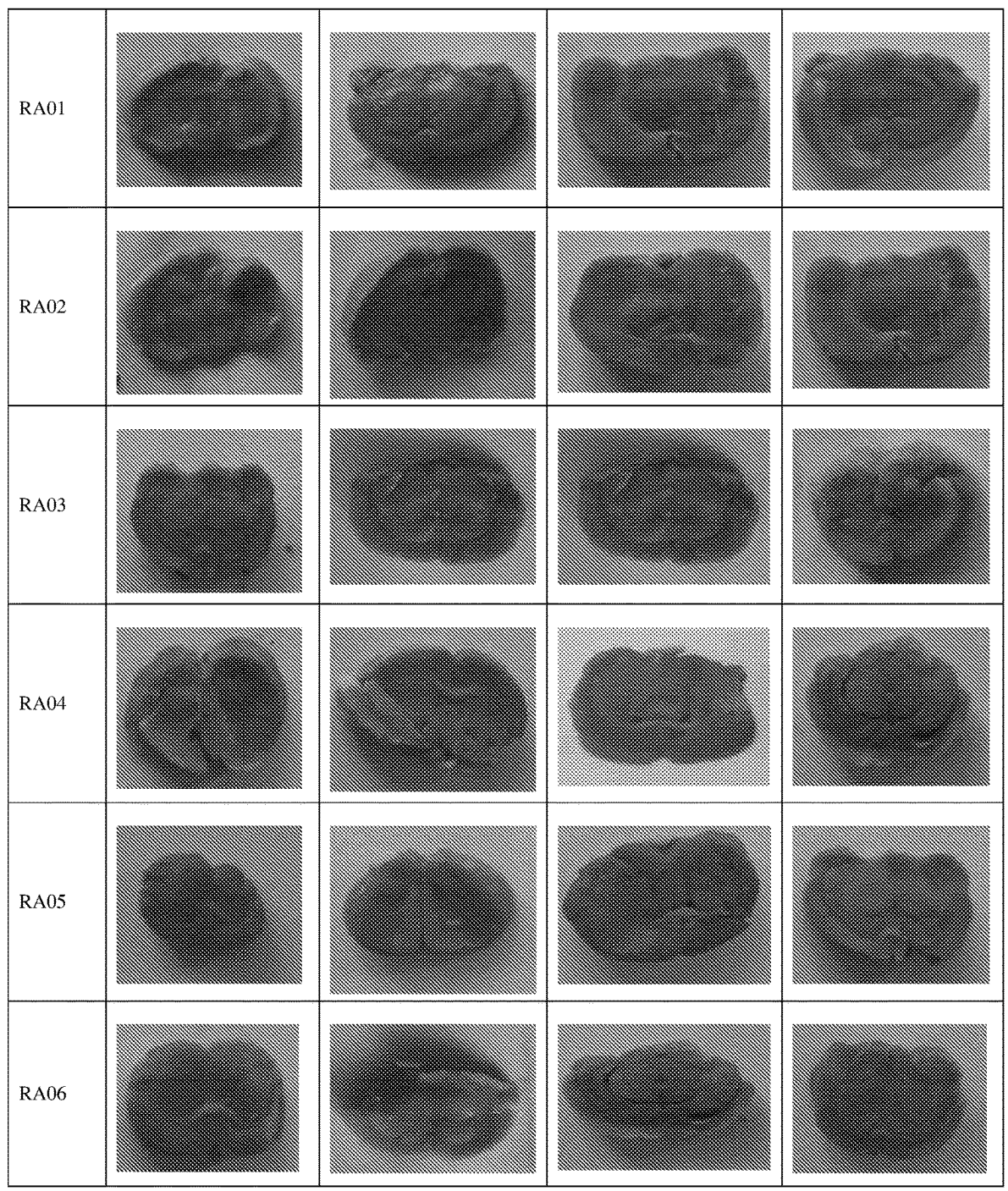
FIG. 6 illustrates the effect of test substances on Rat TTC staining—Group 4-(3-N-butylpthalide (NBP)
Figure 7:
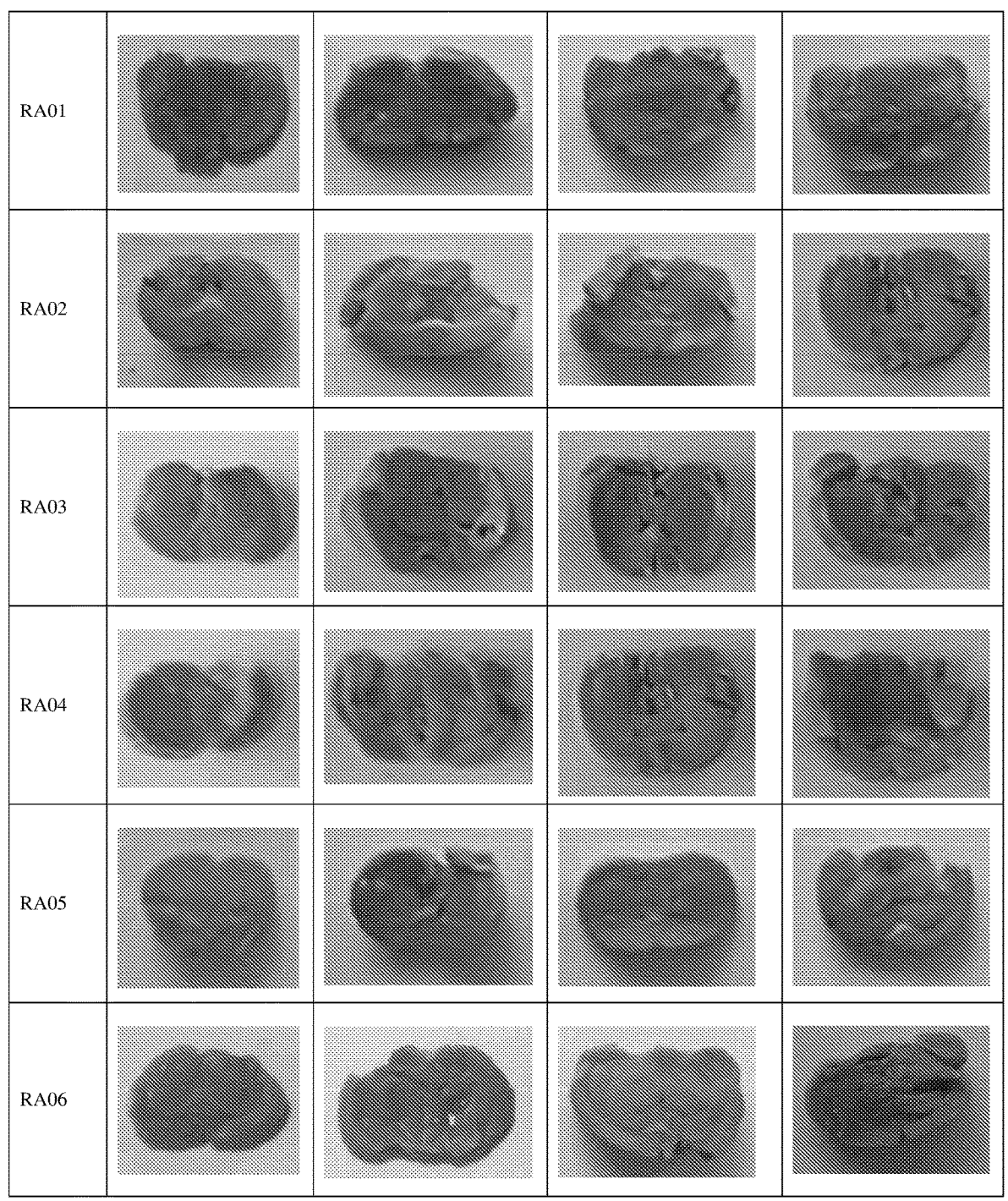
FIG. 7 illustrates the effect of test substances on Rat TTC staining—Group 5-(Nicotinamide Riboside chloride (NR)
Figure 8:
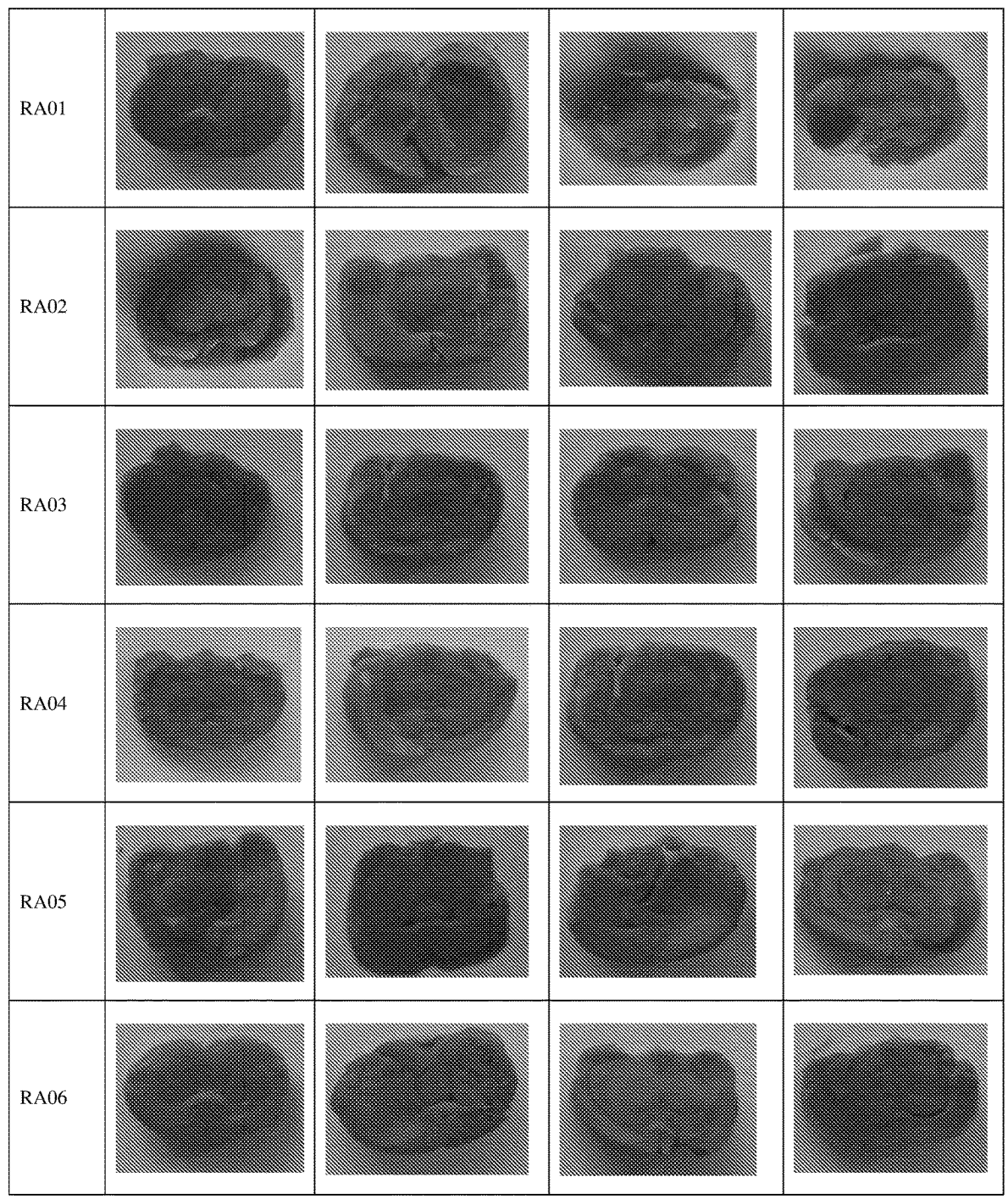
FIG. 8 illustrates the effect of test substances on Rat TTC staining—Group 6- [Combination 3-N-butylpthalide (NBP)+ Nicotinamide Riboside chloride (NR)].

FIG. 5 represents the Tetrazolium chloride staining (TTC) of brain tissue of animals showing normal brain tissue was stained red, whereas ischemic area remained unstained.

CONCLUSION

In the present study, the model of global ischemia reperfusion induced brain injury (cerebral infarction) was performed in rats. The brain infarct area, Biochemical parameters and Histopathology of normal and treated rats with cerebral ischemia or reperfusion injury were investigated to find out how the test substances to protect and improve the brain function. The results showed that these test substances could significantly reduce relative inflammation in brain, and rescue neural dysfunction effectively.

It is concluded that, the test substance i.e., combination of NBP+NR effectively prevents neuron cells from death caused by cerebral ischemia/stroke to protect from brain damage as compared to individual dose of NBP or NR.

We claim:

1. A synergistic nutritional composition consisting of a therapeutically active exogenous combination of:
   10-500 mg of a celery seed extract comprising 90% of Dl-3-N-Butylphthalide (NBP) by weight of the celery seed extract; and
   1-500 mg of nicotinamide riboside chloride, along with pharmaceutically acceptable excipients,
   wherein the synergistic nutritional composition is effective for treating ischemic stroke.

2. The synergistic nutritional composition as claimed in claim 1, wherein the pharmaceutically acceptable excipients are selected from the group consisting of a diluent present in a range of 1 to 30%; a binder present in a range of 0.1 to 25%; a lubricant present in a range of 0.1 to 5.0%; a glidant present in a range of 0.1 to 5.0%; an additive present in a range of 1 to 10%; a surfactant present in a range of 0.1 to 5.0%; and a stabilizer present in a range of 0.1 to 5.0%, by weight of the total composition.

3. The synergistic nutritional composition as claimed in claim 1, wherein an effective unit dose for an oral administration is formulated in a range of 50 to 500 mg.

* * * * *